United States Patent [19]

Okuyama et al.

[11] 4,237,267

[45] Dec. 2, 1980

[54] DISULFIDE COMPOUNDS OF A CARRIER, HAVING S—S EXCHANGE REACTIVITY

[75] Inventors: Tsuneo Okuyama, Yokohama; Tadashiro Fujii, Mishima; Nobuaki Nakagawa; Kikuo Kotani, both of Shizuoka, all of Japan

[73] Assignee: Toyo Jozo Kabushiki Kaisha, Shizuoka, Japan

[21] Appl. No.: 34,861

[22] Filed: Apr. 30, 1979

[30] Foreign Application Priority Data

Apr. 28, 1978 [JP] Japan .................................. 53-49958
Dec. 28, 1978 [JP] Japan ................................. 53-164909

[51] Int. Cl.³ ................. C07C 43/305; C07C 513/00; C07D 519/00
[52] U.S. Cl. ........................................ 536/1; 435/188; 435/192; 435/194; 435/207; 435/815; 546/270; 548/166
[58] Field of Search ............... 546/270; 260/306.5; 536/1; 548/16.6

[56] References Cited

U.S. PATENT DOCUMENTS 2,510,893  6/1950  Kleiman ........................... 260/306.5

FOREIGN PATENT DOCUMENTS 46-4166  3/1968  Japan ...................................... 548/186

OTHER PUBLICATIONS

Wilson, et al., Chem. Abst., vol. 85, abst. 118992h (1976).
Brocklehurst, et al., Biochem. J., vol. 133, pp. 573-584 (1973).
Pharmacia Fine Chemicals, "Activated Thiol-Sepharose 4B," pp. 4-7 and Frontispage, Sweden (1974).
Royer, et al., Chem. Abst., vol. 87, abst. 129,550e (1977).
Chemical Abstracts, Ninth Collective Index (vols. 76-85), Chemical Substances, pp. 35374 CS to 35375 CS.
Chemical Abstracts, vol. 87, p. 4853 CS (1977).

*Primary Examiner*—John D. Randolph
*Attorney, Agent, or Firm*—Young & Thompson

[57] ABSTRACT

A disulfide compound of a carrier, having S—S exchange reactivity, of the formula $$R-S-S-X_1-X_2-A \qquad [I]$$

wherein R is 2-benzothiazolyl, $X_1$ is a spacer group directly bound to the —S—S— and comprises a plurality of carbon atoms in a straight or branched chain, $X_2$ is an imide or amide bonding group, and A is an insoluble carrier selected from the group consisting of beads gel agarose residue, gamma-aminopropylated nylon beads residue and a residual group of partially reduced polyacrylonitrile porous granules or fibers.

3 Claims, 3 Drawing Figures

DISULFIDE COMPOUNDS OF A CARRIER, HAVING S—S EXCHANGE REACTIVITY

This invention relates to a novel disulfide compound of a carrier, having S—S exchange reactivity, of the formula $$R-S-S-X_1-X_2-A \quad [I]$$

wherein R is 2-benzothiazolyl, $X_1$ is a spacer group directly bound to the —S—S— and comprises a plurality of carbon atoms in a straight or branched chain, $X_2$ is an imide or amide bonding group, and A is an insoluble carrier selected from the group consisting of beads gel agarose residue, gamma-aminopropylated nylon beads residue and a residual group of partially reduced polyacrylonitrile porous granules or fibers.

Heretofore, disulfide compounds useful as a carrier for covalent chromatography have been known. Covalent chromatography is used for the separation and purification of compounds having thiol groups for example, enzymes such as papain, urease, β-galactosidase, amino acids such as cysteine, peptides or proteins such as glutathione, albumin, hemoglobin, or cytochrome, or is used for the preparation of immobilizing enzymes, antigens or antibodies.

A disulfide compound of the formula wherein [Sepha] is beads gel agarose residue containing 4% of agarose, is known as activated thiol Sepharose 4B (tradename, Pharamacia Fine Chemicals Co., abbr.: 2-pyridyl-glutathione disulfide, hereinafter designated as 2-PGD-Sepharose 4B). However, the S—S exchange reaction rate of 2-PGD-Sepharose 4B for thiol groups is quite slow and requires a long time, and hence for chromatographical use is disadvantageous.

We have found that a novel disulfide compound of a carrier having S—S exchange reactivity of the formula [I] (hereinafter called as S—S exchange reactive carrier [I] reacts specifically, rapidly and quantitatively with compounds having thiol groups.

The reaction of the S—S exchange reactive carrier [I] of the present invention with a compound having a thiol group is illustrated as follows:

wherein B is the thiol residue of the compound having a thiol group, and R, $X_1$, $X_2$ and A have the same meanings as hereinbefore.

An immobilized enzyme is obtained when that enzyme is used as the thiol compound, and when a hapten, antigen or antibody is used as the thiol compound, an immobilized immune component, useful as a carrier for affinity chromatography for the recovery and purification of solid carriers or immune components, is obtained.

A carrier have a thiol group can also be obtained if the S—S exchange reactive carrier [I] is treated with an S—S bond cleaving reagent such as dithiothreitol or an aqueous solution thereof at pH 9-11 as follows:

wherein R, $X_1$, $X_2$ and A have the same meanings as hereinbefore.

As hereinabove explained, the S—S exchange reactive carrier [I] of the present invention is a novel and useful compound.

An object of the present invention is to provide novel disulfide compounds useful as the S—S exchange reactive carrier [I].

In the disulfide compound useful as the S—S exchange reactive carrier [I], R may be 2-benzothiazolyl or 2-pyridyl-N-oxide and $X_1$ is a spacer group. Examples of the spacer group $X_1$ are carbon chains of 1 to 20 carbon atoms or, except when directly bound to the S—S group, molecular chains up to 20 atoms consisting of carbon, oxygen and nitrogen. The said molecular chain may optionally have amino, carboxyl or hydroxyl groups or these groups protected with protective groups, and optionally be branched or straight. Preferred examples are alkylene groups, or alkylene groups directly bonded terminally to the S—S group and which contain at least one amide group.

In the carrier, $X_2$ is a bonding group, and examples are amides (—CONH—), esters (—COO—), ethers (—O—) or amidino groups.

The said bonding group $X_2$ can be formed by changing a group such as amino, hydroxyl, carboxyl, cyano or nitro in a carrier to its functional group, thereby reacting with the said functional group or its reactive derivative, for example active esters or acid chlorides of carboxyl groups, terminal amination of the said groups by hexamethylenediamine or dodecamethylenediamine, imidation of nitrile groups or amination by reduction of nitrile groups.

A is a bonding residue of a carrier. The carriers include immobilized carriers having at least one functional group such as amino, imino, amide, hydroxyl, carboxyl or nitrile, or having a functional group which can be changed to a reactive derivative. Examples of the said carrier are polysaccharides such as cellulose, amino derivatives of cellulose, dextrine or dextran, or a water insoluble carrier, or a water insoluble carrier having hydroxyl or amino groups such as aminated polyamide, polyacrylonitrile or silane. Also the carriers include either known compounds or novel compounds which can be used as carriers in the present invention. Examples of novel compounds having amino groups are γ-aminopropylated polyamides, amino derivatives of polyacrylonitrile polymers or polyacrylonitrile group polymers. A γ-aminopropylated polyamide is prepared by heating a polyamide carrier such as 6,6-nylon and 6-nylon in γ-aminopropyl triethoxysilane at 100° C. for three hours to introduce partially γ-aminopropyl groups into the amide groups of the polyamide compound. The amino derivatives of polyacrylonitrile polymers or polyacrylonitrile group polymers can be prepared by heat-refluxing a polyacrylonitrile polymer or polyacrylonitrile group polymer in the presence of lithium aluminum hydride in a medium such as diethyl ether, dioxane or tetrahydrofuran for 1-48 hours to form amino groups with partially reduced nitrile groups.

The S—S exchange reactive carrier [I] can be obtained by reacting, for example, a compound of the following formula

[II]

wherein R has the same meanings hereinbefore, such as 2,2′-dithio-bis (benzothiazole) or 2,2-′dithio-bis(pyridine-N-oxide) in an inert solvent such as benzene, toluene, chloroform, carbon tetrachloride, dimethylformamide, acetone, ethanol or methanol or a mixture thereof, with an equimolar amount of a compound of the formula

[III]

wherein $X_3$ is a group which can react with the carrier or a group which can be changed to react with the carrier and $X_1$ has the same meaning hereinbefore, at 10°–70° C. for 10 minutes to 5 hours, and effecting recovery by the known isolating and purification procedures.

The group $X_3$ in a compound of the formula

[IV]

wherein R, $X_1$ and $X_3$ have the same meanings as herinbefore, may optionally be changed to a reactive group which can react with the carrier. Carboxyl groups may be changed to active esters such as succinimide esters or p-nitrophenyl esters or acid chlorides, and nitrile groups may be changed to imidate groups. These reactive group formations can be effected by known activation methods.

Compound [IV] is reacted with the carrier in an inert medium such as water, acetone, ethanol, methanol, dimethylformamide, dioxane or an aqueous solution thereof, under cooling or at ambient temperature for 1 to 40 hours and is filtered and washed to recover the product.

The thus-obtained S—S exchange reactive carrier [I] is a useful and novel compound having a benzothiazole-2′-yl-dithio group or a pyridine-N-oxide-2′-yl-dithio group. The said compound [I] has an S—S exchange activity to combine the carrier with a compound having a thiol group, for example an enzyme such as peroxidase, catalase, β-galactosidase or alkaline phosphatase or hapten, or an antigen and antibody to which a thiol group has been introduced by S-acetylmercapto-succinic anhydride [Arch. Biochem. Biophys., 96, 605–612 (1962)].

A further embodiment of the preparaton of the S—S exchange reactive carrier [I] is as follows:

A thiol agarose compound of the formula (hereinafter called thiol agarose compound [V])

[V]

wherein [A] is an agarose molecule residue, is reacted with a disulfide reagent to prepare the novel disulfide compound of the formula

[I']

The thiol agarose compound [V] can be prepared by a known method [e.g. Biochem. J. 133, 573–584 (1973), or "Practice and Application; Affinity Chromatography", p. 64–65, Kodansha Publisher, 1976 (in Japanese)] or by reducing commercially available activated thiol sepharose with dithiothreitol. As for the agarose molecular residue, an agarose prepared by a known method or commercially available agarose beads gel Sepharose 2B (agarose content: about 2%, swollen grain size: about 60–250μ), tradename, Pharmacia Fine Chemicals Co., Sepharose 4B (agarose content: about 4%, swollen grain size: about 40–190μ) or Sepharose 6B (agarose content: about 6%, swollen grain size: about 40–210μ) can be used. Beads gel agarose (beads gel of water-insoluble three-dimensional structure) is preferably used due to its permeability.

The thiol agarose compound is reacted with a disulfide reagent such as 2,2′-dithio-bis(pyridine-N-oxide) or 2,2′-dithio-bix(benzothiazole) and aqueous ethanol containing EDTA in Tris-HCl buffer with stirring, overnight, and is filtered through a porous glass filter and if required washed with ethanol, benzene or deionized water to obtain the product [I′]. The produce is stored frozen, suspended in 0.1% agarose solution.

Comparisons of S—S exchange reaction rate of compounds having thiol groups, with the compounds of the present invention, and with the known activated thiol Sepharose 4B, are given below. The compounds having thiol groups are glutathione and bovine serum albumin (BSA). The assay method is as follows:

1.5 ml of the disulfide compound [I] or the activated thiol Sepharose 4B in 0.1% agarose is added to 1.45 ml of 1 mM EDTA in 0.2 M Tris-HCl buffer (pH 7.5) or to sodium carbonate buffer (pH 9.5). Thereto is added 50 μl of 10 mM glutathione or 200 μl of 2.5 mM BSA and the increased absorbency per minute for glutathione is measured, or per 20 minutes for BSA at each maximum absorption wave length. The results are shown in Tables 1 and 2.

The following examples non-limitatively illustrate the present invention:

TABLE 1.

| | | (glutathione) | | | |
| --- | --- | --- | --- | --- | --- |
| | | ph 7.5 | | ph 9.5 | |
| | R | wave length (nm) | reaction rate (μmole/min) | wave length (nm) | reaction rate (μmole/min) |
| control |  | 343 | 8.7 | 343 | 28.2 |
| |  | 324 | 52.0 | 287 | 71.9* |
| |  | 276 | 2.2 | 261 | 14.3 |
| present invention |  | 333 | 92.8 | 333 | 131* |

*compensated reaction rate of degradation of disulfide compound at pH 9.5

TABLE 2.

| | | (BSA) | | | |
| --- | --- | --- | --- | --- | --- |
| | | ph 7.5 | | ph 9.5 | |
| | R | wave length (nm) | reaction rate (μmole/min) | wave length (nm) | reaction rate (μmole/min) |
| control |  | 343 | 0.96 | 343 | 7.20 |
| |  | 324 | 1.04 | 287 | 12.8*** |
| |  | 450 | 0.00 | 368 | 7.33 |
| present invention |  | 333 | 3.14 | 333 | 44.7* |
| |  | 310 | 7.65 | 309 | —** |

*compensated reaction rate of degradation of disulfide compound at pH 9.5
**not measured due to rapid degradation of disulfide compound.
***reaction rate calculated by decreased concentration of BSA.

As illustrated in the Tables 1 and 2, the disulfide compounds of the present invention have a higher S—S exchange reaction rate than known disulfides.

EXAMPLE 1

Thiol Sepharose 4B beads (1.6 g, wet weight) of the formula wherein [A'] is beads gel agarose molecule (Sepharose 4B) residue containing about 4% of agarose, are introduced into a 50 ml polyethylene vial, and 10 mM 2,2'-dithio-bis (pyridine-N-oxide) and 50% ethanol containing 1 mM EDTA in 0.2 M Tris-HCl buffer (pH 7.5) (40 ml) are added thereto. After gentle stirring overnight, the reaction mixture is filtered on a porous glass filter, and washed three times with 50% ethanol (40 ml) and five times with deionized water (40 ml) to obtain the disulfide compound wherein [A'] has the same meaning as hereinabove.

Figure 1:
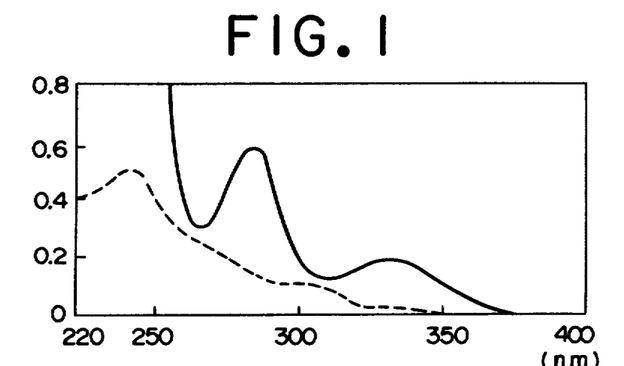

The ultraviolet absorption spectrum of the disulfide compound [I'] in 1.5 ml of 0.2 M Tris-HCl buffer (pH 7.5) containing 1 mM EDTA in 0.1% agarose solution is shown in FIG. 1 (dashed line). Also the absorption spectrum of the reduced form of disulfide compound [I'] by 0.1 M dithiothreitol (50 μl) is shown in FIG. 1 (solid line). 4.85 μmoles of 2-thiopyridine-N-oxide (molecular extinction coefficient 3830 at 333 nm; pH 7.5) per 76.4 mg (dry weight) of the disulfide compound [I'] are liberated, whereby 63.5 μmoles of 2-pyridyl-N-oxide-glutathione disulfide in 1 g (dry weight) of the disulfide compound [I'] are calculated to be present.

EXAMPLE 2

In example 1, 2,2'-dithio-bis (pyridine-N-oxide) is replaced by 2,2'-dithio-bis (benzothiazole) and the remaining procedures are carried out substantially the same as in Example 1. The product is filtered on a porous glass filter, washed three times with ethanol (40 ml), three times with benzol (40 ml), three times with ethanol (40 ml), and five times with deionized distilled water (40 ml) to obtain a compound of the formula wherein [A'] has the same meaning as hereinabove.

Figure 2:
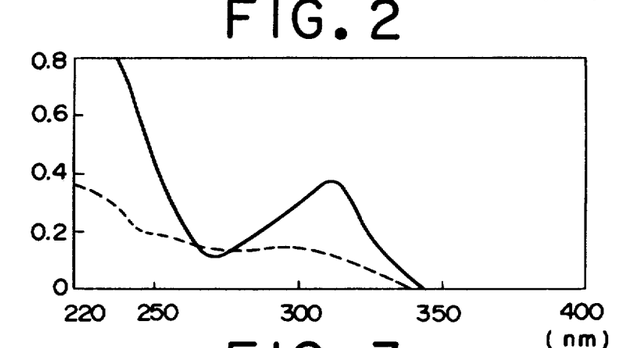

The ultraviolet absorption spectrum of the disulfide compound [I''] and reduced form thereof are shown in FIG. 2 in dashed line and solid line, respectively.

1.88 μmole of 2-thiobenzothiazole (molecular extinction coefficient 19300 at 310 nm) per 60.3 mg (dry weight) of the disulfide compound [I''] is liberated, whereby 31.2 μmoles of 2-benzothiazole-glutathione-disulfide group in 1 g (dry weight) of disulfide [I''] are calculated.

Figure 3:
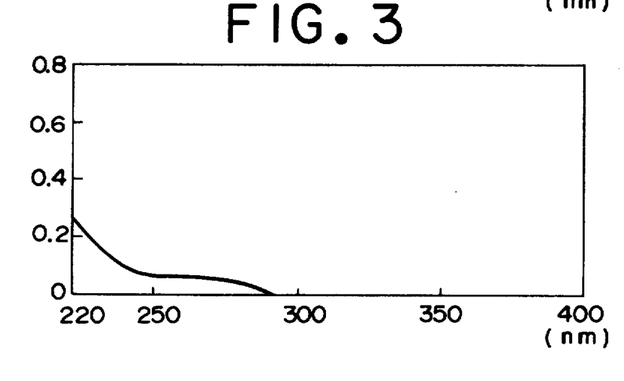

The starting material, thiol Sepharose 4B [V'] hereinbefore is obtained as follows:

2-PGD-Sepharose 4B (Lot No. 3196, Pharmacia Fine Chemicals Co.) (10 g, wet weight) is suspended in 30 mM dithiothreitol and 0.2 M Tris-HCl buffer (pH 7.5) containing 1 mM EDTA. After 20 minutes, the reaction mixture is filtered on a porous glass filter, and the above reaction is repeated for three times in order to complete reduction. Filtration with a porous glass filter is repeated, and then the filtrate is washed with deionized distilled water (100 ml) in order to remove the remaining dithiothreitol to obtain thiol-Sepharose 4B of the formula [V'] hereinbefore. The ultraviolet absorption spectrum of the compound [V'] is shown in FIG. 3.

EXAMPLE 3

6,6-nylon beads (diameter 4.8 mm, 100 g) suspended in γ-aminopropyl triethoxysilane (100 ml) are heated at 100° C. for 3 hours. After heating, the beads are filtered, washed with water and dried to obtain γ-aminopropylated beads.

[γ-aminopropylated ratio per one bead: 54 γ of secondary antibody protein are bound.

Assay method: The above beads in dimethylformamide solution (150 ml) containing succinic anhydride (20 g) are allowed to stand overnight. After filtration and washing, and precipitate is reacted with dicyclohexylcarbodiimide (20 g) and N-hydroxysuccinimide (11.5 g) in dimethylformamide (150 ml) overnight, and is thereafter washed with dimethylformamide.

The obtained beads are washed three times with 0.05 M phosphate buffer (pH 7.4) containing 0.1% NaN₃, 3 mM MgCl₂ and 0.15 M NaCl, and secondary antibody (rabbit's anti-quinea pig IgG: abbr. Ab₂) is added thereto and reacted at 5° C. for 17 hours. The Ab₂-bound beads are obtained after filtration and washing three times with 0.05 M phosphate buffer (pH 7.4) containing 0.1% NaN₃, 0.25% bovine serum albumin, 3 mM MgCl₂ and 0.15 M NaCl (hereinafter called antigen-antibody reaction buffer). To 2 beads thereof are added 1 ml of β-galactosidase cross linked guinea pig's anti-bovine insulin (2 γ), and the mixture is allowed to stand for 20 hours at 5° C., and is thereafter washed with antigen-antibody reaction buffer.

200 μl of reagent for β-galactosidase color reaction, consisting of 5 mg/ml of o-nitrophenylgalactoside in 0.1 M phosphate buffer (pH 6.7) containing 0.1% bovine serum albumin and 10 mM mercaptoethanol are reacted therewith at 44° C. After 20 minutes glycine buffer (pH 10.5, 2.5 ml) is added thereto to stop the reaction and the medium is colorimetrically measured at 420 nm to assay the bound $Ab_2$ by the enzyme immuno assay method.

[β-galactosidase cross-linked anti-bovine insulin is prepared by reacting a dimethylformamide solution of 3-(benzothiazole-2'-yl-dithio) propionate-succinimide ester with 0.1 M veronal buffer solution (pH 7.5) of anti-bovine insulin in equimolar ratio at ambient temperature for 4 hours. The reactant is precipitated by isoelectric precipitation, recovered by centrifugation and dissolved in phosphate buffer (pH 7.5). Thereto is added an equimolar amount of β-galactosidase, and the mixture is reacted at ambient temperature for one hours, then the active fraction is collected with Sephadex G-100 to obtain the cross-linked anti-bovine insulin and β-galactosidase conjugate.]

The γ-aminopropylated beads (20 beads) are added to dimethylformamide (5 ml), and 3-(benzothiazole-2'-yl-dithio) propionate succinimide ester (2.0 mg) in dimethylformamide (1 ml) is added thereto to react at ambient temperature for 4 hours. The reaction mixture is filtered and washed with dimethylformamide—0.1 M phosphate buffer (pH 7.5) to obtain S—S exchange reactive beads carrier into which has been introduced the 3-(benzothiazone-2'-yl-dithio) propionyl group at the γ-amino position.

To these S—S exchange reactive beads is added β-galactosidase (3 mg) in 0.1 M phosphate buffer (pH 7.5), and the mixture is reacted at ambient temperature for 2 hours, and is filtered and washed to obtain immobilized β-galactosidase beads. The product has an activity of 6 units of β-galactosidase per one bead, measured by the β-galactosidase colorimetric reaction.

The above 3-(benzothiazole-2'-yl-dithio) propionate succinimide ester is obtained as follows:

To 2,2'-dithio-bis-(benzothiazole) (13.2 g) is added benzene (400 ml) and 3-mercaptopropionate (6 g), and the mixture is reacted at 70° C. for 3 hours with stirring. Thereafter the reaction mixture is cooled in an ice bath to precipitate the crude crystals (13.8 g) which are recrystallized from benzene to obtain 3-(benzothiazol-2'-yl-dithio) propionate crystals (12 g)

m.p. 162°–164° C.

To this 3-(benzothiazole-2'-yl-dithio)propionate (3 g) in ethyl acetate (200 ml) are added N-hydroxysuccinimide (1 gl) and dicyclohexylcarbodiimide (1.7 g), and the mixture is stirred at ambient temperature for 3 hours. The precipitated dicyclohexylurea is filtered off and the filtrate is washed with phosphate buffer (pH 7.5) to remove unreacted free acid. The ethyl acetate layer is dehydrated by adding anhydrous sodium sulfate, and dried and recrystallized from hot petroleum ether to obtain crystals of 3-(benzothiazole-2'-yl-dithio) propionate succinimide ester (2.4 g)

m.p. 114°–115° C., corrected value: 121°–123° C.

EXAMPLE 4

A porous granular or filamentary substance having free amino and nitrile groups obtained hereinbelow is used in place of γ-aminopropylated beads in Example 3 and the reaction proceeds under the same conditions as described in Example 3 to prepare the granular or filamentary S-S exchange reactive carrier compound in which the 3-(benzothiazole-2'-yl-dithio) propionyl group is introduced into the free amino group.

A 500-ml three-neck flask is placed in a water bath at 35° C. and flushed with nitrogen gas for 15 minutes. Distilled water (120 ml), sodium alkylsulfonate (2 g), acrylonitrile (80 g), sodium persulfate (0.1 g) and sodium hydrogensulfite (0.033 g) are introduced therein, and the mixture is stirred for about 3 hours to obtain an emulsion which is poured into water (500 ml) with sodium chloride added thereto to precipitate the product. The precipitate is filtered, washed with water and air-dried to yield polyacrylonitrile (logarithmic viscosity at 30° C., 0.5% in dimethylformamide: about 10.5). The polyacrylonitrile (10 g) dissolved in dimethylformamide (150 ml) is molded to prepare porous filamentary polyacrylonitrile.

Further polyacrylonitrile (10 g) is dropped into 20% aqueous dimethylformamide using an atomizer cup to prepared porous granular polyacrylonitrile.

Into the three-necked flask, lithium aluminium hydride and dry ether (100 ml) are added with stirring and porous granular polyacrylonitrile (2 g) as produced hereinabove is also added, and the mixture is refluxed at 50° C. for 16 hours; then with ice-cooling, water is added dropwise to decompose unreacted lithium aluminum hydride which is dissolved by adding dropwise 1 N-HCl. An amino derivative of polyacrylonitrile is recovered by filtration, and is washed with 1 N HCl, water, 1 N NaOH, water and 0.1 M phosphate buffer, in this order to obtain a porous granular substance having free amino and nitrile groups.

The porous granular polyacrylonitrile as produced hereinabove is replaced by porous filamentary polyacrylonitrile to obtain a porous filamentary substance having free amino and nitrile groups.

The quantitative assay method for amino groups in these substances is as follows:

The porous substance having free amino and nitrile groups is reacted with 12.5% glutaraldehyde-borate buffer (pH 8.5) at 0° C. for 20 minutes. The reaction mixture is filtered, washed with borate buffer and then added to 7-ADCA (7-aminodesacetoxycephalosporanic acid) in 0.1 M phosphate buffer (pH 7.5) and reacted at 30° C. for 60 minutes with stirring. The amount of 7-ADCA remaining in the supernatant thereof is assayed by liquid chromatography. As a result, it is shown that 33–35 μm of 7-ADCA per gram of porous substance can be bound.

The above glutaraldehyde-treated substance is also treated with 0.2 M hexamethylenediamine (pH 9.5) at room temperature for 2 hours, further reacted with glutaraldehyde, and thereafter reacted with 7-ADCA. The amount of bound 7-ADCA is 42–46 μM/g.

EXAMPLE 5

In Example 3,3-(benzothiazole-2'-yl-dithio) propionate is replaced by 3-(pyridine-N-oxide-2'-yl-dithio) propionate hereinbelow and the reaction proceeds under the same conditions as in Example 3 to obtain an S-S exchange reactive beads substance in which the 3-(pyridine-N-oxide-2'-yl-dithio) propionyl group is introduced into γ-aminopropylated beads.

2,2'-dithio-bis (pyridine-N-oxide) (4.3 g) is added to chloroform (200 ml) and 3-mercaptopropionate (3 g) and the mixture is reacted at 70° C. for 3 hours. The reaction mixture is cooled, and the crude crystals precipitate and are recrystallized from chloroform to obtain crystals of 3-(pyridine-N-oxide-2'-yl-dithio) propionate (4.1 g)

m.p. 126°–218° C.

An active ester, 3-(pyridine-N-oxide-2'-yl-dithio) propionate succinimide ester, is prepared by reaction between the free acid and N-hydroxysuccinimide and dicyclohexylcarbodiimide. uv absorption: λmax=260 nm in methanol, Rf=0.25 (thin layer chromatography, silica gel; benzene:ethyl acetate: 3:1).

EXAMPLE 6

The following illustrated compounds (1)–(29) can be used instead of 3-(benzothiazole-2'-yl-dithio) propionate and 3-(pyridine-N-oxide-2'-yl-dithio) propionate in the foregoing examples.

In the reaction of the said illustrated compounds with the carrier having functional groups which are preferably amino groups, known condensation reactions can be used to obtain the desired S-S exchange reactive carrier compounds.

(1) A mixture of 3-(benzothiazole-2'-yl-dithio) propionate (3 g) obtained by the same preparation process as described in Example 3, and p-nitrophenol (1.2 g) and dicyclohexylcarbodiimide (2.1 g), dissolved in ethyl acetate (20 ml), is stirred at room temperature for 3 hours. The remaining procedure is carried out as in Example 3 to obtain 3-(benzothiazole-2'-yl-dithio) propionate p-nitrophenyl ester (18.5 g) as crystals m.p.: 113°–114° C.

(2) 3-(benzothiazole-2'-yl-dithio) propionate (3 g) dissolved in thionyl chloride (10 ml) is reacted at 25° C. for 2 hours, thereafter thionyl chloride is removed in vacuo to obtain 3-(benzothiazole-2'-yl-dithio) propionyl chloride as an oily substance.

λmax=272 nm (methanol)
Rf=0.25 (TLC, benzene)

(3) 3-(benzothiazole-2'-yl-dithio) propionate succinimide ester (1.3 g) prepared by the same procedure as in Example 3 and ε-aminocaproic acid (0.6 g) are added to tetrahydrofuran (50 ml), and the mixture is reacted at room temperature overnight; the tetrahydrofuran is removed in vacuo, and the medium is thereafter dissolved in hot isopropanol and cooled to obtain crystals of 6-N-[3-(benzothiazole-2'-yl-dithio) propionyl] aminohexanoic acid (0.8 g)

S—S—CH₂—CH₂—CONH—CH₂—(CH₂)₃—CH₂—COOH

λmax=272 nm (in methanol)
Rf=0.07 (TLC silica gel, benzene:ethyl acetate=1:2).

(4) The above-obtained compound (500 mg), N-hydroxysuccinimide (200 mg) and dicyclohexylcarbodiimide (340 mg) dissolved in tetrahydrofuran (10 ml) are reacted at room temperature for 3 hours; the precipitated dicyclohexylurea is filtered off and the tetrahydrofuran is distilled off. The residue is dissolved in hot petroleum ether and cooled to obtain crystals of 6-N-[3-(benzothiazole-2'-yl-dithio)-propionyl] aminohexanate succinimide ester (430 mg)

λmax=271 nm
Rf=0.42 (TLC, silica gel, benzene:ethyl acetate=3:1). (5) 2,2'-dithio-bis (benzothiazole) (1.1 g) and 3-mercaptopropionitrile dissolved in benzene (50 ml) are reacted at 70° C. for 3 hours with stirring. The reaction mixture is cooled in an ice water bath to precipitate the crude crystals which are recrystallized from benzene to obtain 3-(benzothiazole-2'-yl-dithio) propio- nitrile (750 mg). 700 mg thereof is added to a methanol solution (50 ml) containing HCl (19 g) and reacted at 5° C. for overnight, and the solvent is distilled off in vacuo to obtain a crude powder which is washed with benzene to yield methyl 3-(benzothiazole-2′-yl-dithio) propionimidate hydrochloride (720 mg)

λmax=272 nm (methanol)
Rf=0.05 (TLC, silica gel, benzene:ethyl acetate=1:2).

2,2′-dithio-bis (benzothiazole) or 2,2′-dithio-bis (pyridine-N-oxide) as prepared hereinbefore is used together with thioglycolic acid, thiolactic acid, cysteine, thiomalic acid, penicillamine, N-(2-mercaptopropionyl)-glycine or glutathione under the same reaction conditions as hereinbefore and the following compounds are obtained. These compounds can be used for reaction with the carrier having functional groups. In the examples, Rf values are given for silica gel thin layer chromatography.

(6)

λmax=272 nm (methanol)
Rf=0.36 (benzene:methanol=1:2)
S—S exchange reaction rate: 35.6 μmoles/min.

(7)

λmax: 272 nm
Rf: 0.38 (benzene:methanol=1:2)

(8)

λmax: 271 nm (methanol)
Rf: 0.08 (benzene:methanol=1:2); 0.60 (upper layer; butanol:acetic acid:water=4:1:5), (9)

λmax: 271 nm (methanol)
Rf: 0.15 (benzene:ethyl acetate=1:2).

(10)

λmax: 271 nm (pH 7.5, phosphate buffer)
Rf: 0.60 (butanol:acetic acid:water=4:1:5 upper layer).

(11)

λmax: 271 nm (methanol)
Rf: 0.30 (upper layer; butanol:acetic acid:water=4:1:5)
S—S exchange reaction rate: 35.5 μmoles/min.

(12)

λmax: 271 nm, 418 nm (methanol)
Rf: 0.23 (upper layer; butanol:acetic acid:water=4:1:5).

(13)

λmax: 271 nm (methanol)
Rf: 0.48 (benzene:ethyl acetate=3:1).

(14)

λmax: 271 nm (methanol)
Rf: 0.12 (benzene:ethyl acetate=3:1)
S—S exchange reaction rate: 35.0 μmoles/min.

(15)

μmax: 278 nm

Rf: 0.80 (benzene:ethyl acetate=3:1).
(16)

λmax: 271 nm (methanol)
Rf: 0.15 (benzene:ethyl acetate=3:1)
S—S exchange reaction rate: 36.6 μmoles/min.
(17)

λmax: 271 nm (methanol)
Rf: 0.80 (benzene:ethyl acetate=3:1).
(18)

λmax: 271 nm (methanol)
Rf: 0.10 (benzene:ethyl acetate=3:1)
S—S exchange reaction rate: 35.7 μmoles/min.
(19)

λmax: 271 nm (methanol)
Rf: 0.05 (benzene:ethyl acetate=3:1).
(20)

λmax: 272 nm (methanol)
Rf: 0.31 (upper layer; butanol:acetic acid:water=4:1:5)
S—S exchange reaction rate: 35.2 μmoles/min.
(21)

λmax: 270 nm (methanol)
Rf: 0.7 (upper layer; butanol:acetic acid:water=4:1:1)

S—S exchange reaction rate: 92.8 μmoles/min.
(22)

λmax: 270 nm (methanol)
Rf: 0.66 (butanol:acetic acid:water=4:1:1, upper layer)
S—S exchange reaction rate: 93.2 μmoles/min.
(23)

λmax: 310 nm (methanol)
Rf: 0.82 (benzene:ethyl acetate=3:1).
(24)

λmax: 271 nm (methanol)
Rf: 0.41 (butanol:acetic acid:water=4:1:1)
S—S exchange reaction rate: 92.6 μmoles/min.
(25)

λmax: 271 nm (methanol)
Rf: 0.25 (butanol:acetic acid:water=4:1:1)
(26)

λmax: 270 nm (methanol)

Rf: 0.32 (butanol:acetic acid:water=4:1:1)
S—S exchange reaction rate: 90.1 μmoles/min.
(27)

λmax: 270 nm
Rf: 0.20 (butanol:acetic acid:water=4:1:1)
S—S exchange reaction rate: 91.5 μmoles/min.
(28)

λmax: 270 nm
Rf: 0.41 (butanol:acetic acid:water=4:1:1).
(29)

λmax: 270 nm
Rf: 0.25 (butanol:acetic acid:water=4:1:1).

We claim:

1. A disulfide compound of a carrier, having S—S exchange reactivity, of the formula $$R-S-S-X_1-X_2-A \qquad [I]$$

wherein R is 2-benzothiazolyl [or 2-pyridyl-N-oxide], $X_1$ is a spacer group directly bound to the —S—S— and comprises a plurality of carbon atoms in a straight or branched chain, $X_2$ is an imide or amide bonding group, and A is an insoluble carrier selected from the group consisting of beads gel agarose residue, gamma-aminopropylated nylon beads residue and a residual group of partially reduced polyacrylonitrile porous granules or fibers.

2. A disulfide compound of the formula wherein A is beads gel agarose residue.

3. A disulfide compound of the formula wherein A is γ-aminopropylated nylon beads residue or a residual group of partially reduced polyacrylonitrile porous granules or fibers.

* * * * *